United States Patent [19]

Pedersen et al.

[11] Patent Number: 5,840,486
[45] Date of Patent: Nov. 24, 1998

[54] MUTANT DNA ENCODING PROTEIN PHOSPHATASE 1 G-SUBUNIT

[75] Inventors: Oluf Pedersen, Holte, Denmark; Christian Bjørbæk, Boston, Mass.; Lars Hansen, Frederiksberg, Denmark; Patricia Townsend Cohen, Dundee, United Kingdom

[73] Assignee: Novo Nordisk A/S, Bagsvaerd, Denmark

[21] Appl. No.: 537,342

[22] Filed: Oct. 2, 1995

[51] Int. Cl.[6] .......................... C12P 19/34; C07H 21/04; C12N 15/09; C12Q 1/68
[52] U.S. Cl. .......................... 435/6; 435/91.2; 435/252.3; 435/320.1; 435/325; 435/195; 536/23.1; 536/24.3; 530/350; 935/22; 935/66
[58] Field of Search .................................. 536/23.1, 24.3; 435/6, 252.3, 975, 948, 195, 91.2, 320.1, 325; 530/350; 935/22, 66, 68–73, 77, 78

[56] References Cited

PUBLICATIONS

Chen, Y.H., et al., Diabetes, vol. 43, pp. 1234–1241, (1994).
Hansen, L., et al., Human Molecular Genetics, vol. 4, No. 8, pp. 1313–1320 (1995).
Dent, P., et al., Nature, vol. 348, pp. 302–308 (1990).
Kida, Y., et al., Jour. Clin. Invest., vol. 85, pp. 476–481 (1990).
Tang, P.M., et al., Jour. Biol. Chem., vol. 266, No. 24, pp. 15782–15789 (1991).
Vaag, A., et al., J. Clin. Invest., vol. 89, pp. 782–788 (1992).
Schalin–Jäntti, C., et al., Diabetes, vol. 41, pp. 598–604 (1992).
Hubbard, M.J., et al., TIBS 18, pp. 172–177 (1993).

*Primary Examiner*—Stephanie W. Zitomer
*Attorney, Agent, or Firm*—Steve T. Zelson, Esq.; Cheryl H. Agris, Esq.

[57] ABSTRACT

The present invention relates to a mutant DNA sequence encoding protein phosphatase 1 G-subunit, wherein a mutation of G to T occurs in the position of codon 905 of the coding sequence, a method of detecting a mutation in the gene encoding protein phosphatase 1 G-subunit, as well as a diagnostic composition and a test kit for use in the method.

22 Claims, 3 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4322 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGAGCCTTCT    GAAGTACCTA    GTCAGATTAG    CAAAGATAAT    TTTTAGAAG     TTCCTAATTT         60

ATCTGACTCT    CTTTGTGAAG    ATGAAGAAGT    TACTTCCAA     CCTGGTTTCT    CCCCTCAACC        120

AAGTAGACGA    GGTTCTGATT    CTTCTGAAGA    CATATACCTG    GATACCCCAT    CTTCAGGTAC        180

TAGAAGAGTT    TCATTTGCTG    ATTCCTTTGG    ATTCAATCTT    GTGTCTGTTA    AAGAATTTGA        240

TTGCTGGGAA    TTACCGAGTG    CTTCAACCAC    TTTTGACTTA    GGGACGGACA    TTTTCCACAC        300

AGAAGAATAT    GTTTAGCCC     CACTGTTTGA    CTTGCCTTCT    TCAAAAGAAG    ATCTTATGCA        360

ACAACTCCAA    ATACAGAAAG    CAATACTGGA    GTCAACTGAG    TCTCTTCTTG    GGTCTACAAG        420

TATCAAGGGT    ATTATTCGAG    TTTTGAATGT    TTCTTTTGAG    AAGTTAGTAT    ATGTAAGAAT        480

GTCTTTAGAT    GACTGGCAGA    CACATTATGA    CATTTTAGCA    GAATATGTTC    CTAATTCATG        540

TGATGGTGAA    ACTGACCAGT    TCTCCTTTAA    GATTGTATTG    GTTCCTCCTT    ATCAAAAAGA        600

TGGCAGTAAA    GTTGAGTTTT    GTATACGTTA    TGAAACTTCT    GTTGGTACAT    TTTGGTCAAA        660

TAATAATGGC    ACAAATTATA    CATTCATTTG    TCAAAAGAAA    GAACAAGAGC    CGGAGCCTGT        720
```

```
AAAACCATGG  AAAGAAGTTC  CTAACAGACA  AATAAAGGC   TGCTTAAAGG  TAAAATCAAG    780

TAAAGAAGAA  TCATCAGTAA  CATCAGAAGA  AAATAACTTT  GAGAATCCAA  AGAATACAGA    840

TACCTATATC  CCAACAATCA  TTTGTTCTCA  TGAGGACAAG  GAAGATTTGG  AAGCCAGTAA    900

TCGAAATGTA  AAAGATGTAA  ACAGGGAACA  TGATGAACAT  AATGAAAAAG  AATTAGAGTT    960

GATGATAAAT  CAACACTTAA  TAAGAACCAG  AAGTACTGCT  TCCAGAGATG  AAAGGAATAC   1020

ATTTTCAACA  GATCCAGTCA  ATTTTCCAAA  TAAAGCAGAG  GGGTTAGAGA  AGAAGCAAAT   1080

CCATGGTGAA  ATATGTACTG  ACTTGTTCCA  AAGGTCTCTG  TCTCCAAGTT  CATCAGCAGA   1140

AAGCTCCGTA  AAGGGAGATT  TTTACTGCAA  TGAAAAATAT  TCCTCAGGAG  ATGACTGTAC   1200

ACATCAACCT  TCAGAGGAAA  CTACTTCAAA  TATGGGAGAA  ATCAAGCCAT  CATTGGGAGA   1260

TACTAGTAGT  GATGAACTAG  TGCAATTACA  TACTGGCAGC  AAAGAAGTCC  TGGATGATAA   1320

TGCTAATCCA  GCCCATGGCA  ATGGCACAAT  GCAAATACCT  TGCCCCTCTT  CAGATCAACT   1380

AATGGCAGGA  AACCTTAATA  AAAACATGA   AGGAGGAGCT  AAAAAATTG   AAGTAAAAGA   1440

TTTGGGATGT  TTACGAAGAG  ATTTCCATTC  AGATACGTCG  GCATGTCTCA  AAGAATCAAC   1500

AGAAGAAGGA  TCTTCTAAGG  AAGATTATTA  TGGCAATGGT  AAGGATGATG  AAGAACAAAG   1560

AATATATTTA  GGTGTTAATG  AAAAACAAAG  AAAAAATTTC  CAAACAATCT  TACATGACCA   1620

AGAAAGGAAG  ATGGGTAACC  CTAAAATAAG  TGTGGCAGGG  ATTGGAGCTA  GTAACAGAGA   1680

CCTGGCTACT  CTGCTGAGCG  AACATACCGC  AATCCCCACC  CGGGCAATCA  CAGCAGATGT   1740

GTCTCATTCA  CCAAGGACAA  ATTTAAGTTG  GGAAGAAGCT  GTGTTAACCC  CAGAGCATCA   1800

TCATTTGACT  AGTGAAGGCA  GCGCTTTAGG  AGGGATAACT  GGTCAAGTTT  GTTCATCAAG   1860

AACTGGAAAT  GTTTTGAGGA  ATGATTATCT  TTTCCAAGTT  GAAGAAAAAT  CAGGTGGGAT   1920

TAATTCTGAA  GATCAGGATA  ATAGCCCACA  GCATAAACAA  AGTTGGAATG  TTCTGGAAAG   1980

TCAGGGAAAA  TCAAGAGAGA  ATAAGACAAA  CATAACAGAG  CATATCAAAG  GACAAACAGA   2040

TTGTGAAGAC  GTGTGGGGAA  AAAGAGATAA  TACGAGGAGT  TTGAAAGCTA  CTACAGAAGA   2100

ATTGTTTACC  TGCCAAGAAA  CAGTGTGCTG  TGAACTGTCT  TCTCTAGCTG  ATCATGGCAT   2160

TACTGAGAAA  GCAGAAGCTG  GTACAGCCTA  TATAATTAAG  ACAACATCAG  AAAGTACTCC   2220

AGAAAGCATG  TCTGCTAGAG  AAAAAGCAAT  AATTGCTAAG  CTACCTCAAG  AGACAGCACG   2280

AAGTGACAGG  CCCATCGAGG  TAAAGGAAAC  AGCGTTTGAT  CCACATGAAG  GGAGAAATGA   2340

TGATTCACAT  TATACCCTTT  GTCAACGAGA  TACAGTAGGT  GTAATCTATG  ACAATGATTT   2400

TGAAAAGGAA  TCACGTTTAG  GTATTTGTAA  TGTACGTGTA  GATGAAATGG  AGAAGGAAGA   2460

AACCATGTCT  ATGTACAATC  CTAGGAAGAC  ACATGACAGG  GAGAAATGTG  GCACTGGAAA   2520

TATAACATCT  GTGGAAGAAT  CCTCATGGGT  CATTACAGAA  TATCAAAAAG  CAACTTCAAA   2580

ACTGGATTTA  CAGTTGGGAA  TGTTACCAAC  AGACAAAACT  GTATTTCAG   AAAACAGAGA   2640

TCATAGGCAG  GTTCAAGAAT  TATCAAAGAA  AACAGACTCG  GATGCCATTG  TGCATTCTGC   2700

TTTTAACTCA  TACACTAATA  GAGCTCCTCA  GAATAGCTCT  CCTTTTTCCA  AACATCATAC   2760

TGAAATTTCA  GTGTCAACTA  ATGAGCAGGC  AATTGCTGTA  GAGAATGCAG  TTACTACCAT   2820

GGCTAGCCAA  CCTATTTCTA  CGAAATCAGA  AAATATTTGT  AATTCAACAA  GAGAAATCCA   2880

GGGTATTGAG  AAGCACCCTT  ATCCTGAGTC  TAAACCTGAA  GAAGTTTCCA  GAAGTTCAGG   2940

AATAGTGACA  TCAGGTAGTA  GAAAAGAAAG  ATGCATAGGC  CAGATTTTCC  AAACAGAAGA   3000

GTATAGTGTG  GAAAAATCTC  TAGGGCCAAT  GATTTTAATC  AACAAACCTC  TTGAGAATAT   3060

GGAAGAAGCA  AGGCATGAAA  ATGAAGGATT  AGTAAGCTCT  GGGCAATCAC  TATACACTTC   3120
```

-continued

| | | | | | |
|---|---|---|---|---|---|
| AGGTGAAAAG | GAATCTGACA | GCTCTGCTTC | TACTAGTCTT | CCTGTTGAGG | AAAGTCAAGC | 3180
| TCAAGGCAAC | GAATCTTTGT | TTTCAAAATA | TACCAACTCT | AAAATACCTT | ATTTCCTTTT | 3240
| GTTTCTGATA | TTTCTTATAA | CTGTCTACCA | TTATGACTTA | ATGATTGGCT | TGACATTCTA | 3300
| CGTTTTGTCA | TTGTCCTGGC | TATCCTGGGA | AGAGGGTAGA | CAAAAGAGT | CTGTCAAAAA | 3360
| GAAGTAACCT | CAGCACTACT | ATTCTCTCTT | AAAAGATAAG | CTATTTAACC | CCAAACATTT | 3420
| GGATTGGTGA | ATGGGACTAT | TCATTGTTCA | AAGATCCAGT | GCAGTTTTC | TCTTGAAGGA | 3480
| TCATTTAAAA | AGGGACGCGA | ATAAGTTTGC | TCCTTCATAT | AAGTAATTAT | TCTATATAGG | 3540
| ACCATTATGT | TTGGATCATT | AAATACCTAT | ATGAATATGA | GATCTGAAGC | ACGTCAAGTT | 3600
| GAAATTAGGT | ACAGCTGTTG | CTCCTTAGCA | GGCTATGAAG | TTGCAATGCT | TCACATCTCT | 3660
| TCACTACTTA | AAGTGCTATT | TCTTGCATTC | ATTTCTCTTG | CAATAAAGCT | TCATTTTTTT | 3720
| TTCCCCTTGA | GAGTATATAT | TTTCCCCTAC | GGTTTAAAA | AACAGATAAA | ACATGGACAA | 3780
| TGGCAGAGGA | CTTTTTTGGT | CTTTTAGTAT | TGAACATGAA | ATTTGTATTT | AACACTGTAT | 3840
| CATTTATCAG | GATTCATTGA | TCAAATATTT | CAACCTTTTC | ATATTTTAA | GAAAACACCC | 3900
| ATATATATTG | AAATGCAAAC | TTAAACATAT | TCTGTTCACT | TGAGTGTAAT | ACTTGATGCA | 3960
| TGCACACACA | CACACACATA | CCTTCTTTAT | AGCTACAAAG | TCAGGGCGTT | CATAGGCAAA | 4020
| ATCTGACAAG | ACTGAAACAA | TTGGGAGTTA | TCTTTCAATT | CTGAAAAATT | CTGTGGGTGG | 4080
| AATGTCTTTA | AGCAATGCTT | TTCTCTTGTG | AGGGAGACTG | TAACACAGCT | GAACTATTTC | 4140
| AGTTTCAACT | ATTCAGAATT | GAAAATGTAA | ATTAAAATTT | CCACAAGCAT | TGCTTCAGAA | 4200
| TGAATTTGTA | CCTATAAGCA | TAAGGCATTA | AATGACAATA | AAAATTCCAA | ATGGACTATT | 4260
| TGTTCCACAT | TGTATTTTTG | TCTTCAAATA | TTTTCTAAGA | GAATGAATTA | TCCCCCCCGG | 4320
| AA | | | | | | 4322

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TAGGTGAATC TATGACAATG                                                       20

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGTAGAAATA GGTTGGCTAG C                                                    21

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single -continued

```
        ( D ) TOPOLOGY: linear ( i i ) MOLECULE TYPE: DNA (genomic)

( x i ) SEQUENCE DESCRIPTION: SEQ ID NO:4:

ATGGTAGTAA CTGCATTC                                                                18

( 2 ) INFORMATION FOR SEQ ID NO:5:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:5:

CTGGATTTAC AGTTGGGAAT G                                                            21

( 2 ) INFORMATION FOR SEQ ID NO:6:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:6:

CTGGATTTAC AGTTGGGAAT G                                                            21

( 2 ) INFORMATION FOR SEQ ID NO:7:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:7:

CGTAGAAATA GGTTGGCTAG C                                                            21
```

MUTANT DNA ENCODING PROTEIN PHOSPHATASE 1 G-SUBUNIT

FIELD OF THE INVENTION

The present invention relates to a mutant DNA sequence encoding protein phosphatase 1 G-subunit, a method of detecting a mutation in the gene encoding protein phosphatase 1 G-subunit, as well as a diagnostic composition and a test kit for use in the method.

BACKGROUND OF THE INVENTION

The human protein phosphatase 1 (PP1) enzyme complex has been shown to comprise at least three isoforms of the catalytic subunit: PP1Cα, PP1Cβ and PP1Cγ encoded by different genes (13–15). All three subtypes of PP1C exhibit a wide tissue distribution and they all bind to the glycogen associated targeting subunit of PP1 (16). The human G-subunit is probably encoded by a single gene and as determined for rabbit PP1 G-subunit it is expressed in skeletal, heart and diaphragm muscle tissues (17). A different subtype of PP1-G is expressed in liver (1). The rabbit skeletal muscle PP1-G has been shown to undergo in vivo and in vitro phosphorylation at several serine residues most of which are located near the $NH_2$-terminus (for review, see 1). Cyclic AMP-dependent protein kinase phosphorylates PP1 G-subunit at $Ser^{46}$ (site 1) and $Ser^{65}$ (site 2). Phosphorylation of site 2 promotes dissociation of the C-subunit and its translocation from the glycogen-protein particles to the cytosol, where it is likely to be inactivated by a cytosolic protein termed inhibitor-1. Thus, phosphorylation of PP1 G-subunit by cyclic AMP-dependent protein kinase results in an immediate inhibition of glycogen synthesis and a stimulation of glycogenolysis. Insulin stimulates glycogen synthesis and inhibits glycogenolysis in skeletal muscle and this is thought to be mediated by the activation of PP1G as a result of the phosphorylation of site 1 on the G-subunit catalyzed by an insulin stimulated protein kinase (18). The latter was subsequently identified as the Rsk-2 isoform of ribosomal S6 kinase (19) and was also shown to inactivate glycogen synthase kinase-3 (GSK-3) in vitro (20). Since GSK-3 phosphorylates the sites in glycogen synthase which are dephosphorylated in response to insulin, inhibition of GSK-3 by this hormone, which has been demonstrated in vivo (21), may also contribute to the activation of glycogen synthesis. A further complication is that GSK-3 phosphorylates the PP1 G-subunit at $Ser^{38}$ and $Ser^{42}$ in vitro (22), but the relevance of this to insulin action has still to be evaluated.

The glycogen-associated form of protein phosphatase 1 (PP1 G-subunit) derived from skeletal muscle is a heterodimer composed of a 37 kDa catalytic subunit (C) and a 124 kDa targeting and regulatory subunit (G) (1). PP1-G not only binds to muscle glycogen with high affinity and thus enhances dephosphorylation of glycogen bound PP1 substrates such as glycogen synthase and glycogen phosphorylase kinase but also plays an essential role in the control of glycogen metabolism by different hormones (1). Phosphorylation at $Ser^{46}$ (site 1) of the G-subunit in response to insulin enhances the activity of PP1-G towards glycogen bound substrates (stimulation of glycogen synthesis and inhibition of glycogenolysis) while phosphorylation at $Ser^{65}$ (site 2) of PP1-G in response to adrenaline causes dissociation of PP1C from the targeting G-subunit thereby inhibiting glycogen synthesis and stimulating glycogenolysis (1).

In subsets of patients with widespread disorders like obesity, non-insulin dependent diabetes mellitus (NIDDM), essential hypertension, dyslipidemia, and premature atherosclerosis, impaired insulin stimulated non-oxidative glucose disposal, which primarily reflects insulin resistance of skeletal muscle glycogen synthesis, has repeatedly been reported (2,3). Resistance to the action of insulin on muscle glycogen synthesis has therefore been proposed as the inherited basis for subsets of disorders in the insulin resistance syndrome. In support of this hypothesis, defective insulin mediated activation of muscle glycogen synthase has been found in glucose tolerant but insulin resistant first degree relatives of Caucasian NIDDM patients (4,5). Also in severely insulin resistant Pima Indians a reduced basal and insulin stimulated activity of protein phosphatase 1 in muscle tissue has been demonstrated, providing a mechanism by which glycogen synthase activation by insulin is reduced in these subjects (6,7).

Obviously, numerous genes encoding proteins participating in insulin signaling and glucose processing in muscle may be involved in the pathogenesis of insulin resistance and given the heterogeneity of disorders the inherited component of the impaired insulin stimulated glycogen synthesis may well comprise a series of different genes. Previously, several candidate genes have been examined for mutations including insulin receptor substrate-1 (IRS-1) (8), insulin sensitive glucose transporter Glut 4 (9), insulin stimulated protein kinase-1 (10), three catalytic subunits of PP1-C (10) and glycogen synthase (9). Except for two non-conservative amino acid polymorphisms in IRS-1 (8) no frequent mutations have been found. The gene which encodes the G-subunit of PP1 was therefore considered a possible candidate for inherited insulin resistance of muscle glycogen synthesis. The human PP1 G-subunit cDNA has recently been cloned (11). Applying Single Strand Conformation Polymorphism (SSCP) scanning of the PP1 G-subunit cDNA a heterozygous missense mutation ($Ala^{931} \rightarrow Glu$) in one out of 30 insulin resistant NIDDM patients (11). The carrier of this mutation had an insulin stimulated non-oxidative glucose metabolism in the lower part of the range for NIDDM patients compatible with a defect in the insulin activation of the PP1 G-subunit (11).

SUMMARY OF THE INVENTION

The gene encoding the PP1 G-subunit was investigated for further mutations by heteroduplex formation analysis (12) resulting in the identification of a mutation in codon 905.

Accordingly, the present invention relates to a DNA isolate comprising a DNA sequence encoding the protein phosphatase type 1 (PP1) G-subunit, the DNA sequence containing a mutation of G to T in the first position of codon 905 such that aspartic acid$^{905}$ in the expressed PP1 G-subunit is substituted by tyrosine, or comprising a fragment of the DNA sequence spanning said mutation.

The aspartic acid to tyrosine polymorphism at codon 905 of PP1 G-subunit has been found to occur with a genotype prevalence of 13% in the examined group of 313 NIDDM patients and 18% in the examined group of 150 healthy Danish Caucasians. Studies in a subgroup of healthy subjects applying the euglycemic hyperinsulinemic clamp technique in combination with indirect calorimetry demonstrate that this allelic variation of PP1 G-subunit has functional importance in that carriers of this mutation have been found to exhibit insulin resistance of non-oxidative glucose metabolism as well as an increased basal glucose oxidation rate. The individuals who were heterozygous for the $Asp^{905}/Tyr^{905}$ polymorphism had, on average, a 54% increase in whole body basal glucose oxidation rate and a 26% reduction in insulin stimulated nonoxidative glucose disposal rate compared to homozygous Asp$^{905}$ individuals. A case-control study of 313 NIDDM patients and 150 controls showed that the prevalence of the PP1 G-subunit Tyr$^{905}$ variant allele was similar in NIDDM and control subjects.

The results obtained in apparently healthy individuals suggest, that the PP1 G-subunit variant is associated with an increased whole body glucose oxidation in the fasting state as well as an impaired nonoxidative glucose metabolism after 4 h of euglycemia and hyperinsulinemia. In this context it is of interest that studies in rat skeletal muscle have provided experimental evidence that under basal insulin conditions a large portion of the intracellular glucose-6-phosphate (G6P) is derived from glycogen rather than from plasma glucose (23). In addition, experiments in the same animal model demonstrated that skeletal muscle glycogenolysis is more sensitive to insulin than is glucose uptake and glycogen synthesis (23). Therefore, the present finding of an increased glucose oxidation rate in Tyr$^{905}$ subunit carriers may in part be secondary to a diminished ability of the mutant PP1 G-subunit to mediate the inhibitory effect of fasting insulin on glycogen breakdown in peripheral tissues thereby causing elevated intracellular levels of G6P for glucose oxidation. Alternatively and/or additionally an increased glycogenolysis might be caused by an enhanced sensitivity to β-adrenergic stimulation of mutant PP1 G-subunit (1).

The surprising finding that the Tyr$^{905}$ PP1 G-subunit associates with a whole body insulin resistance which is specific for the glycogen synthesis pathway of peripheral tissues is compatible with a diminished effect of insulin on the mutant PP1 G-subunit and consequently a reduced activation of glycogen synthesis. It has been recognized for a long time that whole body insulin sensitivity is affected by both nongenetic components (i.e. physical activity and diet) and genetic factors, the latter elucidated in studies of genetic admixture and familial transmission in various ethnic groups (24,25). The genetics behind the physiologic variation in the population is at present unknown. In this connection, the Asp$^{905}$/Tyr$^{905}$ polymorphism of the PP1 G-subunit offers the first important contribution to explain the large variation in insulin stimulated glycogen synthesis of peripheral tissues in the general Caucasian population.

In another aspect, the present invention relates to a living system containing a DNA isolate of the invention and capable of expressing the PP1 G-subunit wherein Asp$^{905}$ is substituted by Tyr. The living system, which may comprise a cell or a multicellular organism containing the appropriate signal transduction pathway, may be used to screen for substances which have an effect on insulin resistance of non-oxidative glucose metabolism.

In a further aspect, the present invention relates to a method of detecting the presence of a mutation of G to T in the first position of codon 905 of the gene encoding the PP1 G-subunit, the method comprising obtaining a biological sample from a subject and analyzing the sample for said mutation. Based on current knowledge, it is assumed that this method may be used to diagnose predisposition to insulin resistance of non-oxidative glucose metabolism in a subject as well as other disorders resulting from insulin resistance, such as obesity, essential hypertension, dyslipidemia or premature atherosclerosis. Furthermore, it cannot be excluded that the Tyr$^{905}$ PP1 G-subunit variant may act in combination with mutations in other insulin resistance genes to present a significant risk for the onset of some subtypes of NIDDM.

Biological samples may, for instance, be obtained from blood, serum, plasma or tissue.

The invention further relates to a diagnostic composition and a test kit for use in the method.

DETAILED DESCRIPTION OF THE INVENTION

In a preferred embodiment, the DNA isolate of the invention comprises the DNA sequence shown in the Sequence Listing as SEQ ID NO:1, in which the G to T mutation occurs in nucleotide 2711.

The length of the DNA isolate may vary widely depending on the intended use.

For use as an oligonucleotide probe for hybridization purposes, the DNA fragment may be as short as 17 nucleotides. For expression in a living system as defined above, the DNA isolate will typically comprise the full-length DNA sequence encoding the PP1 G-subunit mutant.

The DNA isolate of the invention comprising the mutation of G to T in the first position of codon 905 in the DNA sequence encoding the PP1 G-subunit may suitably be of genomic or cDNA origin, for instance obtained by preparing a genomic or cDNA library and screening for DNA sequences coding for all or part of the PP1 G-subunit by hybridization using synthetic oligonucleotide probes in accordance with standard techniques (cf. Sambrook et al., Molecular Cloning: A Laboratory Manual, 2nd Ed., Cold Spring Harbor, 1989). The probes used should be specific for the mutation. Alternatively, the DNA sequence encoding wild-type PP1 G-subunit may be modified by site-directed mutagenesis using synthetic oligonucleotides containing the mutation for homologous recombination in accordance with well-known procedures.

The DNA sequence may also be prepared by polymerase chain reaction (PCR) using specific primers, for instance as described in U.S. Pat. No. 4,683,202, or Saiki et al., *Science*239, 1988, pp. 487–491, or *PCR Protocols*, 1990, Academic Press, San Diego, Calif. USA.

The DNA isolate of the invention may also be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed and ligated. This procedure may preferably be used to prepare fragments of the PP1 G-subunit encoding DNA sequence.

The recombinant vector into which the DNA isolate is inserted may be any vector which may conveniently be subjected to recombinant DNA procedures. The choice of vector will often depends on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated (e.g. a viral vector).

The recombinant vector is preferably an expression vector in which the DNA sequence encoding the PP1 G-subunit mutant is operably connected to additional segments required for transcription of the DNA. In general, the vector is derived from plasmid or viral DNA or may contain elements of both. The term "operably linked" indicates that the segments are arranged so that they function in concert for their intended purposes, e.g. transcription initiates in a promoter and proceeds through the DNA sequence coding for the PP1 G-subunit mutant.

The promoter may be any DNA sequence which shows transcriptional activity in the host cell of choice and may be derived from genes encoding proteins either homologous or heterologous to the host cell. Examples of suitable promoters for directing the transcription of the mutant DNA encoding IRS-1 in mammalian cells are the SV40 promoter (Subramani et al., Mol. Cell Biol. 1 (1981), 854–864), the MT-1 (metallothionein gene) promoter (Palmiter et al., Science 222 (1983), 809–814) or the adenovirus 2 major late promoter.

The mutant DNA sequence encoding the PP1 G-subunit may also be operably connected to a suitable terminator, such as the human growth hormone terminator (Palmiter et al., op. cit.). The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector may further comprise a DNA sequence enabling the vector to replicate in the host cell in question. An example of such a sequence is the SV40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for the PP1 G-subunit, the promoter and the terminator, respectively, and to insert them into suitable vectors containing the information necessary for replication, are well known to persons skilled in the art (cf., for instance, Sambrook et al., op. cit.).

In a further aspect, the present invention relates to a variant of the PP1 G-subunit in which aspartic acid$^{905}$ is substituted by tyrosine, or a fragment thereof containing said substitution.

The living system into which the DNA isolate of the invention is introduced may be a cell which is capable of producing the PP1 G-subunit and which has the appropriate signal transduction pathways. The cell is preferably a eukaryotic cell, such as a vertebrate cell, e.g. a *Xenopus laevis* oocyte or mammalian cell, in particular a mammalian cell. Examples of suitable mammalian cell lines are the COS (ATCC CRL 1650), BHK (ATCC CRL 1632, ATCC CCL 10), CHL (ATCC CCL 39) or CHO (ATCC CCL 61) cell lines. Methods of transfecting mammalian cells and expressing DNA sequences introduced in the cells are described in e.g. Kaufman and Sharp, J. Mol. Biol. 159 (1982), 601–621; Southern and Berg, J. Mol. Appl. Genet. 1 (1982), 327–341; Loyter et al., Proc. Natl. Acad. Sci. USA 79 (1982), 422–426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841–845.

The mutant DNA sequence encoding the PP1 G-subunit may then be expressed by culturing a cell as described above in a suitable nutrient medium under conditions which are conducive to the expression of the PP1 G-subunit-coding DNA sequence. The medium used to culture the cells may be any conventional medium suitable for growing mammalian cells, such as a serum-containing or serum-free medium containing appropriate supplements. Suitable media are available from commercial suppliers or may be prepared according to published recipes (e.g. in catalogues of the American Type Culture Collection).

The living system according to the invention may also comprise a transgenic animal. A transgenic animal is one in whose genome a DNA sequence encoding the PP1 G-subunit mutant has been introduced. In particular, the transgenic animal is a transgenic nonhuman mammal, mammals being generally provided with appropriate signal transduction pathways. For the present purpose, it is generally preferred to employ smaller mammals, e.g. rodents such as mice, rabbits or rats.

For expression of the PP1 G-subunit mutant in transgenic animals, a mutant DNA sequence encoding the PP1 G-subunit mutant is operably linked to additional DNA sequences required for its expression to produce expression units. Such additional sequences include a promoter as indicated above, as well as sequences providing for termination of transcription and polyadenylation of mRNA. Construction of the expression unit for use in transgenic animals may conveniently be done by inserting a DNA sequence encoding the mutant PP1 G-subunit into a vector containing the additional DNA sequences, although the expression unit may be constructed by essentially any sequence of ligations.

The expression unit is then introduced into fertilized ova or early-stage embryos of the selected host species. Introduction of heterologous DNA may be carried out in a number of ways, including microinjection (cf. U.S. Pat. No. 4,873,191), retroviral infection (cf. Jaenisch, Science 240, 1988, pp. 1468–1474) or site-directed integration using embryonic stem cells (reviewed by Bradley et al., *Bio/Technology* 10, 1992, pp. 534–539). The ova are then implanted into the oviducts or uteri of pseudopregnant females and allowed to develop to term. Offspring carrying the introduced DNA in their germ line can pass the DNA on to their progeny, allowing the development of transgenic populations.

General procedures for producing transgenic animals are known in the art, cf. for instance, Hogan et al., *Manipulating the Mouse Embryo: A Laboratory Manual*, Cold Spring Harbor Laboratory, 1986; Simons et al., *Bio/Technology* 6, 1988, pp. 179–183; Wall et al., *Biol. Reprod.* 32, 1985, pp. 645–651; Buhler et al., *Bio/Technology* 8, 1990, pp. 140–143; Ebert et al., *Bio/Technology* 6: 179–183, 1988; Krimpenfort et al., *Bio/Technology* 9: 844–847, 1991, Wall et al., *J. Cell. Biochem.* 49: 113–120, 1992; U.S. Pat. No. 4,873,191, U.S. Pat. No. 4,873,316; WO 88/00239, WO 90/05188; WO 92/11757 and GB 87/00458. Techniques for introducing heterologous DNA sequences into mammals and their germ cells were originally developed in the mouse. See, e.g. Gordon et al., *Proc. Nad. Acad. Sci. USA* 77: 7380–7384, 1980, Gordon and Ruddle, *Science* 214: 1244–1246, 1981; Palmiter and Brinster, *Cell* 41: 343–345, 1985; Brinster et al., *Proc. Natl. Acad. Sci. USA* 82: 4438–4442, 1985; and Hogan et al. (ibid.). In brief, in the most efficient route used to date in the generation of transgenic mice, several hundred linear molecules of the DNA of interest are injected into one of the pronuclei of a fertilized egg according to techniques which have become standard in the art. Injection of DNA into the cytoplasm of a zygote can also be employed. Similar procedures may be employed for the production of transgenic individuals of other species.

In one embodiment of the present method of detecting the presence of the mutation of G to T in the first position of codon 905 of the PP1 G-subunit gene, a biological sample is obtained from a subject, DNA (in particular genomic DNA) is isolated from the sample and digested with a restriction endonuclease which cleaves wild-type PP1 G-subunit DNA at a recognition site eliminated by the mutation of G to T in the first position of codon 905 of the PP1 G-subunit gene so that the mutant PP1 G-subunit DNA is not cleaved at this site, and the PP1 G-subunit DNA is analyzed for cleavage at this site.

After digestion, the resulting DNA fragments may be subjected to electrophoresis on an agarose gel. The restriction pattern obtained may be analyzed, e.g. by staining with ethidium bromide and visualizing bands in the gel by means of UV light. The restriction pattern of the DNA after digestion with the restriction endonuclease may then be compared to the restriction pattern obtained with a negative control comprising at least a portion of wild-type DNA encoding the PP1 G-subunit spanning codon 905, and/or with a positive control comprising at least a portion of DNA encoding the PP1 G-subunit and containing the mutation. For instance, the number and size of restriction fragments may be compared on the agarose gel, from which carriers of the mutation may be identified, and from which heterozygous carriers may be distinguished from homozygous carriers.

An example of a suitable restriction endonuclease is Dde 1 which has the recognition sequence CTNAG, cutting after C (at position 2707 of the PP1 G-subunit gene) and leaving a 3 base 5' overhang. This recognition sequence is abolished by the mutation of G to T in position 2711.

In a variant of this embodiment, the DNA isolated from the sample may be amplified prior to digestion with the restriction endonuclease. Amplification may suitably be performed by polymerase chain reaction (PCR) using oligonucleotide primers based on the appropriate sequence of PP1 G-subunit spanning the site(s) of mutation, essentially as described by Saiki et al., *Science* 230, 1985, pp. 1350–1354. After amplification, the amplified DNA may be digested with the appropriate restriction endonuclease and subjected to agarose gel electrophoresis. As a control, wild-type DNA encoding the PP1 G-subunit (i.e. not containing the mutation) may be subjected to the same procedure, and the restriction patterns may be compared.

A further embodiment of the method of the invention is an adaptation of the method described by U. Landegren et al., *Science* 241, 1988, pp. 1077–1080, which involves the ligation of adjacent oligonucleotides on a complementary target DNA molecule. Ligation will occur at the junction of the two oligonucleotides if the nucleotides are correctly base paired.

In a still further embodiment of the present method, the DNA isolated from the sample may be amplified using oligonucleotide primers corresponding to segments of the gene coding for the PP1 G-subunit. The amplified DNA may then be analyzed by hybridization with a labelled oligonucleotide probe comprising a DNA sequence corresponding to at least part of the gene encoding the PP1 G-subunit and containing the mutation of G to T in the first position of codon 905. As a control, the amplified DNA may furthermore be hybridized with a labelled oligonucleotide probe comprising a DNA sequence corresponding to at least part of the wild-type gene encoding the PP1 G-subunit spanning codon 905. This procedure is, for instance, described by DiLella et al., *Lancet* 1, 1988, pp. 497–499. Another PCR-based method which may be used in the present invention is the allele-specific PCR method described by R. Saiki et al., *Nature* 324, 1986, pp. 163–166, or D. Y. Wu et al., *Proc. Natl. Acad. Sci. USA* 86, 1989, pp. 2757–2760, which uses primers specific for the mutation in the PP1 G-subunit gene.

Other methods of detecting mutations in DNA are reviewed in U. Landegren, *GATA* 9, 1992, pp. 3–8. A currently preferred method of detecting mutations is by single stranded conformation polymorphism (SSCP) analysis substantially as described by Orita et al., *Proc. Natl. Acad. Sci. USA* 86, 1989, pp. 2766–2770, or Orita et al., *Genonics* 5, 1989, pp. 874–879.

The mutation may also be detected by heteroduplex formation analysis. Heteroduplex formation scanning is a technique that utilizes the formation of DNA heteroduplexes from alleles differing at one or a few nucleotides during the multiple denaturation-annealing steps in normal PCR-amplifications (12). During non-denaturing gel electrophoresis the normal double stranded homoduplex DNA segments migrate at a different speed than their heteroduplex counterparts. Thus, heterozygous carriers of mutations in a specifically amplified gene may be identified as having two bands of double stranded DNA instead of one. Homozygous mutation carriers, however, cannot be detected by this technique because no heteroduplexes are formed.

The label substance with which the oligonucleotide probe is labelled is preferably selected from the group consisting of enzymes, colored or fluorescent substances, or radioactive isotopes.

Examples of enzymes useful as label substances are peroxidases (such as horseradish peroxidase), phosphatases (such as acid or alkaline phosphatase), β-galactosidase, urease, glucose oxidase, carbonic anhydrase, acetylcholinesterase, glucoamylase, lysozyme, malate dehydrogenase, glucose-6-phosphate dehydrogenase, β-glucosidase, proteases, pyruvate decarboxylase, esterases, luciferase, etc.

Enzymes are not in themselves detectable but must be combined with a substrate to catalyze a reaction the end product of which is detectable. Examples of substrates which may be employed in the method according to the invention include hydrogen peroxide/tetramethylbenzidine or chloronaphthole or o-phenylenediamine or 3-(p-hydroxyphenyl) propionic acid or luminol, indoxyl phosphate, p-nitrophenylphosphate, nitrophenyl galactose, 4-methyl umbelliferyl-D-galactopyranoside, or luciferin.

Alternatively, the label substance may comprise colored or fluorescent substances, including gold particles, colored or fluorescent latex particles, dye particles, fluorescein, phycoerythrin or phycocyanin.

In a particularly favored embodiment, the probe is labelled with a radioactive isotope. Radioactive isotopes which may be used for the present purpose may be selected from I-125, I-131, In-111, H-3, P-33, C-14 or S-35. The radioactivity emitted by these isotopes may be measured in a beta- or gamma-counter or by a scintillation camera in a manner known per se.

For use in the present method, the invention further relates to a test kit for detecting the presence of a mutation of G to T in the first position of codon 905 of the gene encoding the PP1 G-subunit, the kit comprising (a) a restriction endonuclease which cleaves wild-type PP1 G-subunit DNA at a recognition site eliminated by the mutation of G to T in the first position of codon 905 of the PP1 G-subunit gene so that the mutant PP1 G-subunit DNA is not cleaved at this site, (b) a first DNA sequence corresponding to at least part of the wild-type gene encoding the PP1 G-subunit spanning codon 905 and/or (c) a second DNA sequence corresponding to at least part of the gene encoding the PP1 G-subunit and containing a mutation of G to T in the first position of codon 905.

The first DNA sequence may, for instance, be obtained from genomic DNA or cDNA encoding the PP1 G-subunit obtained from a healthy subject (a non-mutation carrier). The second DNA sequence may conveniently be a DNA isolate according to the invention.

For use in the present method, the invention further relates to a test kit for detecting the presence of a mutation of G to T in the first position of codon 905 of the gene encoding the PP1 G-subunit, the kit comprising (a) means for amplifying DNA, and (b) a labelled oligonucleotide probe comprising a DNA sequence corresponding to at least part of the gene encoding the PP1 G-subunit and containing a mutation of G to T in the first position of codon 905.

Appropriate means for amplifying DNA (typically genomic DNA isolated from the biological sample) include, for instance, oligonucleotide primers, appropriate buffers and a thermostable DNA polymerase.

The test kit may further comprise a labelled oligonucleotide probe comprising a DNA sequence corresponding to at least part of the wild-type gene encoding the PP1 G-subunit spanning codon 905.

The invention is further illustrated in the following example which is not intended in any way to limit the scope of the invention as claimed.

BRIEF DESCRIPTION OF THE DRAWINGS

The present invention is described in detail with reference to the appended drawings, wherein.

EXAMPLE

Materials and Methods

Subjects

Figure 1A:
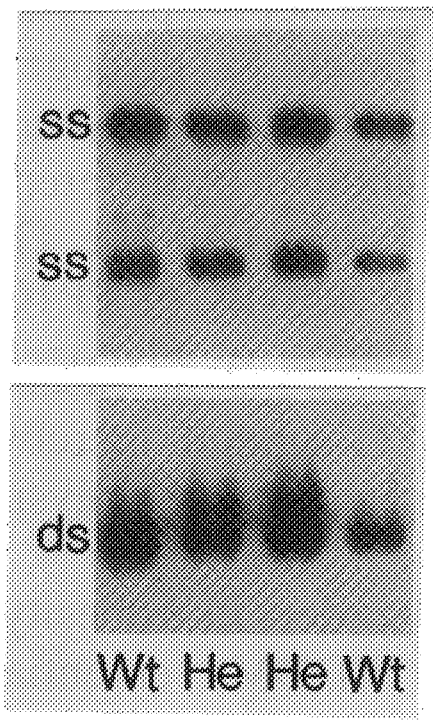
FIG. 1a is an autoradiogram showing heteroduplex formation in the double stranded DNA bands (ds) corresponding to the nucleotide 2584–2844 cDNA segment of the human PP1 G-subunit from two heterozygous subjects (lanes 2,3) compared to wild types (lanes 1,4).

Heteroduplex formation scanning was carried out in 30 NIDDM patients on whom we previously performed SSCP scanning of the coding region of the PP1 G-subunit gene (11). These Danish Caucasian diabetic patients were insulin resistant (11) as estimated by the euglycemic hyperinsulinemic clamp technique and all had a fasting serum C-peptide level above 0.3 nM. The NIDDM patients were treated with diet alone or with a combination of diet and oral hypoglycemic drugs.

An association study was performed in 313 NIDDM patients (mean age 55±8 yr) and 150 healthy control subjects without known predisposition of NIDDM (mean age 53±10 yr). The NIDDM patients (109 females, 204 males) had an average diabetes duration of 6.3 years (±6.1 yr), fasting plasma glucose of 10.7 mM (±3.6 mM) and $Hb_{A1c}$ of 8.3% (±1.7%). The control subjects (62 females, 88 males) had an average fasting plasma glucose of 4.9 mM (±0.6 mM) and a $Hb_{A1c}$ of 5.4% (±0.5%). Twenty-seven of the 150 healthy controls volunteered for a euglycemic hyperinsulinemic clamp investigation in combination with indirect calorimetry to relate the values of whole body glucose metabolism to the PP1 G-subunit genotype. Prior to the participation in the investigation the purpose and risks of the study were carefully explained both vocally and in writing to all study participants and their informed consent was obtained. The protocol was approved by the committee of ethics in Copenhagen and was in accordance with the Helsinki Declaration.

Euglycemic hyperinsulinemic clamp

The 27 healthy subjects who were examined did not differ in phenotype characteristics from those who did not participate in the clamp protocol. The studies were initiated in the morning at 8.00 a.m. after a 10 h overnight fast. Each clamp comprised of a 2 h basal period followed by a 4 h hyperinsulinemic, euglycemic clamp. Details of the clamp technique have been described previously (27). To assess total peripheral glucose uptake, (3-$^3$H) glucose was infused throughout the study period. Tritiated glucose was administered as a primed (25 $\mu$Ci) continuous (0.25 $\mu$Ci/min) infusion. The clamp was performed by continuous infusion of 2 mU insulin·kg$^{-1}$·min$^{-1}$ (Actrapid, Novo Nordisk A/S, Bagsværd, Denmark), and euglycemia was maintained by a variable infusion of 20% glucose at a rate determined by measurement of the plasma glucose concentration at 5- to 10-min intervals. Total glucose disposal rate was calculated from the plasma concentrations of [3-$^3$H]glucose and plasma glucose with Steele's non-steady state equations (28). In these calculations, the distribution volume of glucose was taken as 200 ml/kg body weight and the pool fraction as 0.65. At the highest steady-state level, where the hepatic glucose production is nil, glucose infusion rates were used to calculate the glucose disposal rate.

Glucose and lipid oxidation

Indirect calorimetry was performed using flow-through canopy gas analyzer system (Deltatrac Metabolic Monitor, Datex, Helsinki, Finland). After an equilibration period of 10 min, the average gas exchange rates recorded over the two 30 min steady state periods were used to calculate rates of glucose oxidation and lipid oxidation. Protein oxidation rate was estimated from urea nitrogen excretion (1 g nitrogen=6.25 g protein). Rates of oxidation were calculated from Frayn's equation (29). The nonoxidative glucose metabolism was calculated as the difference between the total glucose disposal rate and the glucose oxidation rate as determined by indirect calorimetry.

Heteroduplex formation analysis

Heteroduplex formation scanning is a technique that takes advantage of the formation of DNA heteroduplexes from alleles differing at one or a few nucleotides during the multiple denaturation-annealing steps in normal PCR-amplifications (12). The formation of heteroduplexes can be facilitated if the PCR-amplification is terminated with inclusion of a final denaturation step followed by slowly cooling to ambient temperature. Alternatively, the PCR products in loading buffer can be heat-denatured followed by cooling on ice for 10 min immediately prior to loading on the gel.

During non-denaturing gel electrophoresis the normal double stranded homoduplex DNA segments migrate at a different speed than their heteroduplex counterparts. Thus, heterozygous carriers of mutations in a specifically amplified gene can be identified as having two bands of double stranded DNA instead of one. Homozygous mutation carriers, however, cannot be detected by this technique because no heteroduplexes are formed. Since we have used a denaturing loading buffer we could also detect single stranded DNA during electrophoresis. In our hands this method has also proved successful in previous studies (8).

Heteroduplex formation scanning was carried out after segmental PCR amplification of PP1 G-subunit cDNA in 15 different overlapping segments with the overlaps varying from 16 to 78 bp as described previously (11) but with the addition of a final denaturation step in the PCR reaction at 99° C. for 10 min followed by slowly cooling to ambient temperature. One $\mu$l of the reaction mixture was mixed with 3 $\mu$l of sequencing stop solution (0.3M NaOH, 0.1M EDTA, 10% glycerol, and 0.03% xylene cyanol/bromphenol blue). This mixture was loaded onto 38 (height)×31 (width)×0.03 cm 5% polyacrylamide gel (49:1, acrylamide:bisacrylamide) in 90 mM Tris-borate, 2.5 mM EDTA, with 5% glycerol. Electrophoresis was carried out at room temperature (25°–29° C.) powered by a temperature controlling device (Stratagene, La Jolla, Calif.). The gels were tranfsferred to a 3 MM filter paper, covered with plastic wrap, and autoradiographed at −80° C. with intensifying screens for 8–12 h (FIG. 1a).

Isolation of genomic DNA from blood

Genomic DNA was isolated from human leucocyte nuclei isolated from whole blood by proteinase K digestion followed by phenol-chloroform extraction on an Applied Biosystems 341 Nucleic Acid Purification System (Foster City, Calif.).

Isolation of total RNA from human skeletal muscle

In the fasting state at 0800 after an overnight fast a percutaneous biopsy (about 500 mg) of vastus lateralis muscle was taken under local anesthesia (1% lidocaine without epinephrine) about 20 cm above the knee using a modified Bergstrom needle. Muscle biopsies were homogenized in a 4M guanidinium thiocyanate solution, and subsequently total RNA was isolated on an Applied Biosystems 341 Nucleic Acid Purification System (Applied Biosystems Inc., Foster City, Calif.).

Oligonucleotides used for amplification

Oligonucleotides, 20–22 mers in length, were synthesized on an Applied Biosystems 394 DNA/RNA Synthesizer and purified on a NAB™-10 column (Pharmacia P-L Biochemicals Inc., Milwaukee, Wis.). Fluorescein labeling of primers were done during synthesis using the FluorePrime™ Amidite (Pharmacia).

cDNA synthesis cDNA was synthesized in volumes of 25 $\mu$l containing (in final concentrations) 50 mM Tris-HCl (pH 8.3), 75 mM KCl, 3 mM MgCl$_2$, 10 mM DDT, 0.2 mM dNTP's, 40 units of RNasin (Promega, Madison, Wis.), 0.625 micrograms of Oligo (dT)$_{18}$, 400 units of MMLV RT (Life Technologies Inc., Grand Island, N.Y.) and 1.0 $\mu$g of total muscle RNA. The reactions were performed at 37° C. for 1 h, followed by enzyme inactivation during 10 min incubation at 95° C.

Direct DNA sequencing

Single stranded DNA for sequencing was generated by using biotinylated oligonucleotide primers and streptavidine-coated magnetic beads according to the manufacturer's recommendations (Dynal A/S Oslo, Norway). PCR reactions were performed with 5 pmol of biotinylated primers. Dideoxynucleotide sequencing using sequenase 2.0 (United States Biochemical Corporation, Cleveland, Ohio) and ($\alpha$-$^{35S}$) dATP (Amersham International plc, Buckinghamshire, Great Britain) was performed according to standard procedures. Heteroduplex forming PCR segments were sequenced on both strands by amplifying a biotinylated 2378–2844 segment and use of nested sequencing primers (b=biotin):

PCR primers:

$_{2378}$TAGGTGAATCTATGACAATG$_{2398}$ (SEQ ID No:2)

$_{2844}$bCGTAGAAATAGGTTGGCTAGC$_{2824}$ (SEQ ID NO:3)

Sequencing primers:

$_{2822}$ATGGTAGTAACTGCATTC$_{2805}$ (SEQ ID NO:4)

$_{2584}$CTGGATTTACAGTTGGGAATG$_{2604}$ (SEQ ID NO:5)

Amplification of genomic DNA

Each PCR-reaction was carried out with 100 ng of genomic DNA as template. The assay conditions were: 10 mM Tris-HCl (pH 9.0), 50 mM KCl, 1.5 mM MgCl$_2$, 0.1% Triton X-100, 0.2 mM dNTP's, 0.2 $\mu$M of each oligonucleotide primer and 0.6 unit of eaq DNA polymerase (Promega), all in final concentrations and 25 $\mu$l reaction volumes. The mixture was overlaid with 18 $\mu$l of mineral oil and after initial denaturation at 95° C. for 3 min, the samples were subjected to 40 cycles of amplification: annealing at 55° C. for 1 min, extension at 72° C. for 1 min and denaturation at 94° C. for 1 min. Oligonucleotide primers used to amplify nucleotide segment 2584–2844 were (the A-primer was fluorescein labeled)

PP1G-A: $_{2584}$CTGGATTTACAGTTGGGAATG$_{2604}$ (SEQ ID NO:6)

PP1G-B: $_{2844}$CGTAGAAATAGGTTGGCTAGC$_{2824}$ (SEQ ID NO:7)

Restriction fragment length polymorphism (RFLP)

Dde 1 restriction enzyme (New England Biolabs, Inc., Me.) digestion of PCR amplified nucleotide fragment 2584–2844 was carried according to manufacturer's recommendations: five $\mu$l PCR reaction mixture was digested by 2–4 U Dde 1 in a total volume of 15 $\mu$l at 37° C. for 4–8 h. This reaction mixture was mixed with an equal volume of stop buffer (formamide with 5 mg/l dextran blue), denatured at 90° C. for 3 min and subsequently loaded onto a 6% denaturing acrylamide PreMix Long Ranger (HydroLink, AT Biochem, Pa.) on an automated laser fluorescence DNA sequencer (Pharmacia). This type of gel can be repetitively loaded 6 times.

Figure 2:
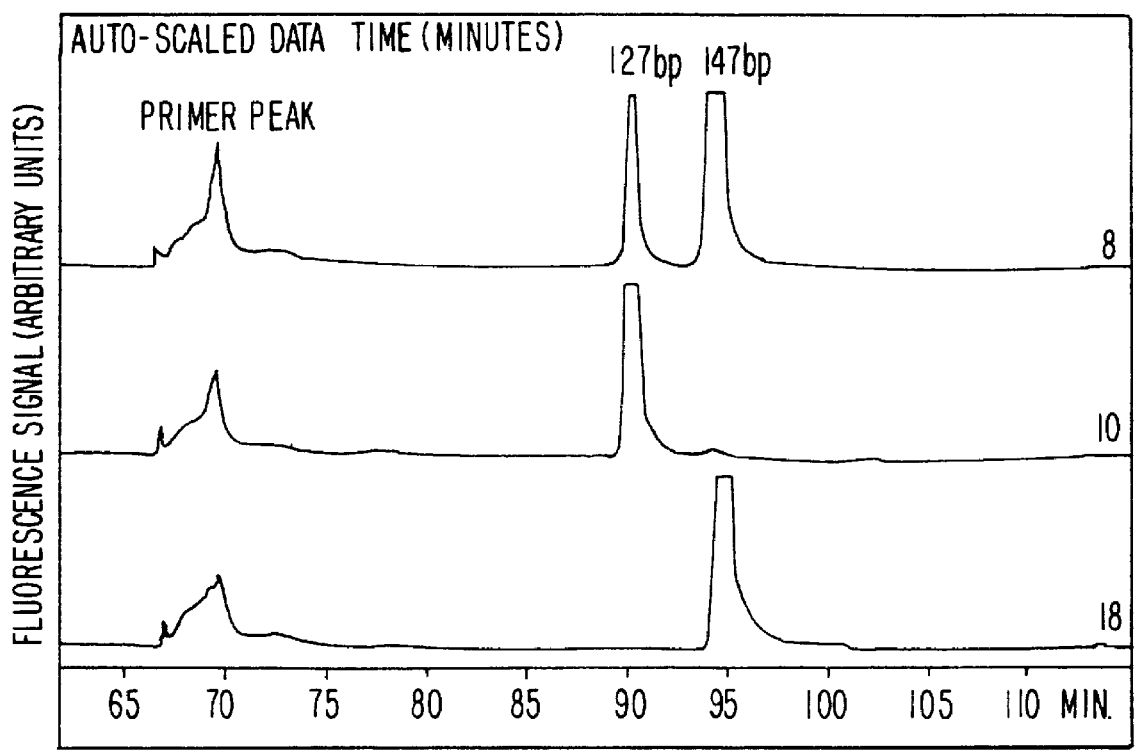
FIG. 2 is a print from an automated laser fluorescence DNA sequencer using the "DNA fragment manager" software. The RFLP examples of the three different genotypes are visible as peaks of fluorescence. Upper lane (8) shows a heterozygous ($G^{2713} \rightarrow T$) RFLP consisting of a 127 and a 147 bp. fragment, middle lane (10) shows the wild type ($G^{2713}$) RFLP with one 127 bp. fragment, and bottom lane (18) shows a homozygous ($G^{2713} \rightarrow T$) RFLP with one 147 bp. fragment.

The 2584–2844 nt DNA segment of PP1 G-subunit contains two cutting sites for Dde 1 restriction enzyme at base positions 2709 and 2729, respectively. The recognition sequence is C↓TNAG cutting after the C and leaving a 3 base 5'primed overhang. The change of a G$^{2713}$→T deletes this Dde 1 recognition site in the PP1 G-subunit segment 2584–2844. Dde 1 digestion of the wild-type 2584–2844 DNA segment results in three DNA fragments of 127 bp, 115 bp, and 20 bp, respectively, whereas a heterozygous carrier will generate four different DNA fragments of 147 bp, 127 bp, 115 bp, and 20 bp. A homozygous carrier of the G$^{2713}$→T mutation will generate two DNA fragments of 147 bp and 115 bp. When the DNA segment is fluorescein labeled in the 5'-end, electrophoresis on an automated laser fluorescence DNA sequencer will reveal a wild type as one single peak corresponding to the 127 bp fragment, whereas a heterozygote will appear as two peaks corresponding to the 127 bp and 147 bp fragments. A homozygote for the $T^{2713}$ will appear as one peak corresponding to the 147 bp fragment (FIG. 2).

Other analyses

Glucose in plasma and urine was measured by a hexokinase method. Serum insulin and C-peptide concentrations were analyzed by RIA (30,31). HbAlc was measured by a HPLC method, normal range 4.1–6.1%. Body fat mass was measured with an impedance technique (32) and fat free mass was calculated by substrating fat mass from body mass.

Statistics

Chi-square analysis was applied to test for significance of differences in allelic frequencies among NIDDM patients and matched controls. The Mann-Whitney U test was used for comparison of unpaired data. Data are means±SE. P<0.05 was considered significant.

RESULTS

Heteroduplex formation analysis and nucleotide sequencing

Figure 1B:
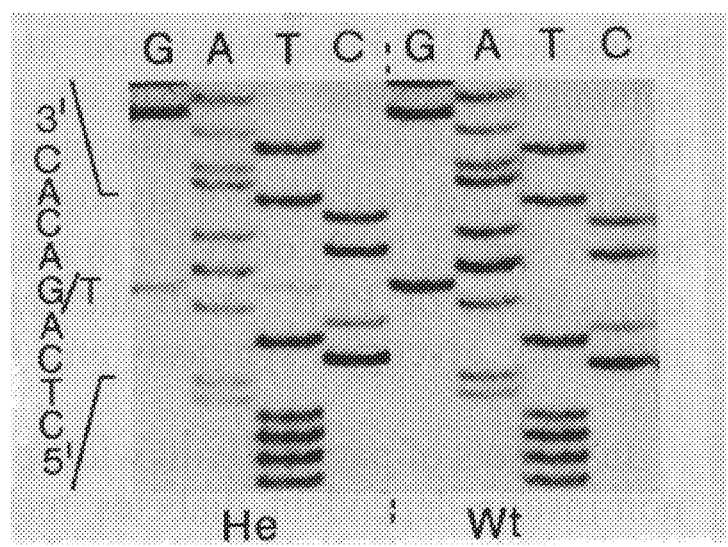
FIG. 1b is an autoradiogram with sequence ladder of a part of the PP1 G-subunit cDNA segment 2378–2844 of the coding strand showing the $G^{2713} \rightarrow T$ mutation in a heterozygous carrier (lane 1) compared to the wild type sequence (lane 2). This predicts a codon change: $Asp^{905} \rightarrow Tyr$.

When 15 overlapping segments of the PP1 G-subunit cDNA were examined in 30 NIDDM patients two cases of heteroduplex formation were identified in the same 2584–2844 nt. PCR segment (FIG. 1a). Nucleotide sequencing revealed that both patients were heterozygous carriers of the same $G^{2713} \rightarrow T$ mutation encoding an $Asp^{905} \rightarrow Tyr$ amino acid substitution (FIG. 1b).

Studies of whole body glucose metabolism

To study the potential influence of the $Tyr^{905}$ substitution on whole body glucose metabolism, 27 healthy control subjects, who volunteered for a 4 h euglycemic hyperinsulinemic clamp in combination with indirect calorimetry, were examined. PP1-G genotyping showed that 6 individuals were heterozygous for the $Asp^{905}/Tyr^{905}$ polymorphism and 21 were wild type ($Asp^{905}$) carriers. The two groups did not differ statistically regarding age, body mass index, fat free mass, fasting level of plasma glucose or fasting serum levels of insulin and C-peptide (Table 1). Furthermore, the two groups of volunteers did not differ significantly in basal or insulin stimulated whole body glucose disposal rates (Table 1). Importantly, however, the routing of glucose in whole body metabolism differed in the $Tyr^{905}$ carriers when compared to the wild type carriers. Thus, basal glucose oxidation was significantly increased by 54% (p<0.04) whereas insulin stimulated nonoxidative glucose metabolism was decreased significantly by 25% (p<0.04) in mutation carriers.

Association study

By means of RFLP analysis as described in Methods and depicted in FIG. 2 an association study was performed in 313 NIDDM patients and 150 control subjects. Four of the NIDDM patients were homozygous (ho=1%) for the $Tyr^{905}$ substitution and 37 were heterozygous (he=12%) for the same mutation whereas 272 were wild types (wt=87%). Among the controls, one subject was homozygous (ho=1%) and 26 were heterozygous (he=17%) whereas 123 were wild types (wt=82%). The genotype (ho+he) frequency in NIDDM patients (13%) did not differ significantly from the genotypic frequency in control subjects (18%). ($X^2$=1.94, p=0.16).

References

1) Hubbard M. J. and Cohen P. (1993) On target with a new mechanism for the regulation of protein phosphatase. TIBS 18, 172–177.
2) Reaven G. M. (1988) Role of insulin resistance in human disease. Diabetes 37, 1595–1607.
3) Beck-Nielsen H. and Groop L. C. (1994) Metabolic and genetic characterization of prediabetic states. J. Clin. Invest. 94, 1714–1721.
4) Vaag A., Henriksen J. E., Beck-Nielsen H. (1992) Decreased insulin activation of glycogen synthase in skeletal muscle muscles in young nonobese Caucasian first-degree relatives of patients with non-insulin dependent diabetes mellitus. J. Clin. Invest. 89, 782–8.
5) Schalin-Jantii C., Harkonen M., Groop L. C. (1992) Impaired activation of glycogen synthase in people at risk for developing NIDDM. Diabetes 41, 598–604.
6) Kida Y., Raz I., Maeda R., Nyomba B. L., Bogardus C., Sommercorn J., Mott D. M. (1992) Defective insulin response of phosphorylase phosphatase in insulin-resistant humans. J. Clin. Invest. 89, 610–617.
7) Kida Y., Esposito-Del Puente A., Bogardus C., Mott D., M. (1990) Insulin resistance is associated with reduced fasting and insulin-stimulated glycogen synthase phosphatase activity in human skeletal muscle. J. Clin. Invest. 85, 476–481.
8) Almind K., Bjørbæk C., Vestergaard H., Hansen T., Echwald S., Pedersen O. (1993) Amino acid polymorphisms of insulin receptor substrate-1 in non-insulin-dependent diabetes mellitus. Lancet 342, 828–832.
9) Bjørbæk C., Echwald S. M., Hubricht P., Vestergaard H., Hansen T., Zierath J., Pedersen O. (1994) Genetic variants in promoters and coding regions of the muscle glycogen synthase and the insulin responsive Glut 4 genes in NIDDM. Diabetes 43, 976–983.
10) Bjørbæk C., Vik T., Echwald S. M., Pei-Yi Yang., Vestergaard H., Wang J. P., Webb G. C., Richmond K., Hansen T., Erikson R. L., Gabor Miklos G. L., Cohen P. T. W., Pedersen O. (Jan 1995) Cloning of a human insulin-stimulated protein kinase (ISPK-1) gene and analysis of coding regions and mRNA levels of the ISPK-1 and the protein phosphatase-1 genes in muscle from NIDDM patients. Diabetes in press.
11) Chen Y. H., Hansen L., Chen M. X., Bjørbæk C., Vestergaard H., Hansen T., Cohen P. T. W., Pedersen O. (1994) Sequence of the human glycogen-associated subunit of type 1 protein phophatase and analysis of its coding region and mRNA level in muscle from patients with NIDDM. Diabetes 43, 1234–1241.
12) Ravnik-Glavac M., Glavac D., Dean M. (1994) Sensitivity of single-strand conformation polymorphism and heteroduplex method for mutation detection in the cystic fibrosis gene. Hum. Mol. Genet. 3; 5; 801–807.
13) Barker H. M., Jones T. A., da Cruz e Silva E. F., Spurr N. K., Sheer D., Cohen P. T. W. (1990) Localization of the encoding a type 1 protein phosphatase catalytic subunit to human chromosome band 11q13. Genomics 7, 159–166.
14) Barker H. M., Brewis N. D., Street A. J., Spurr N. K., Cohen P. T. W. (1994) Three genes for protein phosphatase 1 map to different human chromosomes: Sequence, expression and gene localization of protein serine/threonine phosphatase 1 beta (PP1CB). Biochem Biophis Acta. 1220, 212–218.
15) Barker H. M., Craig S. P., Spurr N. K., Cohen P. T. W. (1993) Sequence of protein serine/threonine phosphatase 1 gamma and localization of the gene (PP1CC) encoding it to chromosome bands 12q24. 1-q24.2. Biochem Biophis Acta. 1178, 228–233.
16) Alessi, D. R., Street, A. J., Cohen, P. T. W. (1993) Inhibitor-2 functions like a chaperone to fold three expressed isoforms of mammalian protein phosphatase-1 into a conformation with the specificity and regulatory properties of the native enzyme. Eur. J. Biochem. 213, 1055–1066.

17) Tang P. M., Bondor J. A., Swidereck K. M., DePaolli-Roach A. A. (1991) Molecular cloning and expression of the regulatory R(GI) subunit of the glycogen associated protein phosphatase. J. Biol. Chem. 266, 15782–15789.
18) Dent P., Lavoinnne A., Nakielny S., Caudwell F. B., Watt P., Cohen P. (1990) The molecular mechanism by which insulin stimulates glycogen synthesis in mammalian skeletal muscle. Nature 348, 302–308.
19) Sutherland C., Campbell D. G., and Cohen P. (1993) Identification of insulin stimulated protein kinase-1 as the rabbit equivalent of rsk$^{-mo}$-2. Eur. J. Biochem. 212, 581–588.
20) Sutherland C., Leighton I. A., Cohen P. (1993) Inactivation of glycogen synthase kinase 3β by phosphorylation: New kinase connections in insulin and growth factor signaling. Biochem. J. 296, 15–19.
21) Cross, D. A. E., Alessi, D. R., Vandenheede, J. R., McDowell, H. E., Hundal, H. S., and Cohen, P. (1994) The inhibition of glycogen synthase kinase-3 by insulin or insulin-like growth factor 1 and the rat skeletal muscle cell line L6 is blocked by wortmannin, but not by rapamycin:evidence that wortmannin blocks activation of the mitogen-activated protein kinase pathway in L6 cells between Ras and Raf. Biochem. J. 303, 21–36.
22) Dent, P., Campbell, D. G., Hubbard, M. J., and Cohen, P. (1989) Multisite phosphorylation of the glycogen-binding subunit of protein phosphatase-1G by cyclic AMP-dependent protein kinase and glycogen synthase kinase-3. FEBS Lett. 248, 67–72.
23) Rosetti L., and Hu M. (1993) Skeletal muscle glycogenolysis is more sensitive to insulin than is glucose transport/phosphorylation. J. Clin. Invest. 92, 2963–2974.
24) Hamman R. F. (1992) Genetic and environmental determinants of non-insulin dependent diabetes mellitus (NIDDM). Diabetes Metab. Rev. 8, 287–338.
25) Hansen B. C. (1993) Genetics of insulin action. Bailliere's Clin. Endocr. Metab. 7, 1033–1061.
26) Martin B. C., Warran J. H., Krolewski A. S., Bergman R. N., Soeldner J. S., Kahn C. R. (1992) Role of glucose and insulin resistance in the development of type 2 diabetes mellitus: results of a 25 year follow-up study. Lancet 340, 925–929.
27) DeFronzo R. A., Tobin J. D., Andres R. (1979) Glucose clamp technique: a method for quantifying insulin secretion and resistance. Am. J. Physiol. 237, E214–E223.
28) Steele R. (1959) Influence of glucose loading and of injected insulin on hepatic glucose production. Ann. N.Y. Acad. Sci. 82, 420–430.
29) Frayn K. N. (1983) Calculation of substrate oxidation rates in vivo from gaseous exchange. J. Appl. Physiol. 55, 628–634.
30) Heding L. G. (1972) Determination of total serum insulin (IRI) in insulin-treated diabetic patients. Diabetologia 8, 260–266.
31) Heding L. G. (1975) Radioimmunological determination of human C-peptide in serum. Diabetologia 11, 541–548.
32) Heitman B. L. (1990) Prediction of body water and fat in adult Danes from measurements of electrical impedance. A validation study. International Journal of Obesity 14, 789–802.

We claim:

1. A DNA isolate comprising a DNA sequence encoding the protein phosphatase type 1 (PP1) G-subunit, wherein said coding sequence of PP1 G-subunit is mutated in the first position of codon 905 such that aspartic acid$^{905}$ in the expressed PP1 G-subunit is substituted by tyrosine; or a fragment of said DNA isolate spanning codon 905 that specifically hybridizes to the complement of said DNA isolate.

2. The DNA isolate according to claim 1, wherein said DNA sequence is SEQ ID NO:1, which sequence contains a T in nucleotide 2711; or a fragment of SEQ ID NO:1 spanning said mutation that specifically hybridizes to the complement of SEQ ID NO:1.

3. A recombinant vector comprising the DNA isolate according to claim 1.

4. A host cell transfected with a DNA isolate according to claim 1.

5. A method of detecting the presence of a mutation of G to T in the first position of codon 905 of the gene encoding the PP1 G-subunit, comprising obtaining a biological sample from a human subject and analyzing the biological sample for said mutation.

6. The method according to claim 5, wherein the biological sample is analyzed by isolating DNA from said sample; digesting said DNA with a restriction endonuclease which cleaves wild-type PP1 G-subunit DNA at a codon 905 containing recognition site but does not cleave mutant DNA at said recognition site, wherein said mutant DNA contains a T in the first position of codon 905 of the PP1 G-subunit coding sequence; and analyzing a restriction pattern obtained from said digestion.

7. The method according to claim 6, wherein said restriction pattern is compared to a second restriction pattern obtained by digesting wild-type DNA encoding PP1 G-subunit spanning codon 905.

8. The method according to claim 6, wherein said restriction pattern is compared to a second restriction pattern obtained by digesting mutant DNA encoding PP1 G-subunit and spanning codon 905, wherein said mutant DNA contains T in the first position of codon 905 of the PP1 G-subunit coding sequence.

9. The method according to claim 6, wherein the restriction endonuclease is Dde 1.

10. The method according to claim 6, further comprising amplifying said isolated DNA prior to digestion with said restriction endonuclease.

11. The method according to claim 6, wherein the biological sample is analyzed by isolating DNA from said sample, amplifying said DNA, hybridizing said DNA to a labeled oligonucleotide probe that specifically hybridizes to mutant DNA containing a T in the first position of codon 905 of PP1 G-subunit coding sequence.

12. The method according to claim 5, wherein said amplified DNA is further hybridized to a labeled oligonucleotide probe spanning codon 905 of PP1 G-subunit coding sequence, that specifically hybridizes to wild-type PP1 G-subunit coding sequence DNA.

13. The method according to claim 12, wherein said label bound to said oligonucleotide probe specific for said mutant PP1 G-subunit DNA is different from the label bound to said oligonucleotide probe specific for wild-type PP1 G-subunit DNA.

14. The method according to claim 12, wherein said label is selected from the group consisting of enzymes, colored or fluorescent substances, and radioactive isotopes.

15. The method according to claim 5, wherein the biological sample is analyzed by isolating DNA from said sample, amplifying said DNA, and subjecting said amplified DNA to heteroduplex formation analysis to determine the presence of a mutation of G to T in a DNA segment spanning codon 905 of the PP1 G-subunit coding sequence.

16. A method for determining predisposition to insulin resistance/reduced insulin-stimulated non-oxidative glucose metabolism in a subject comprising detecting the presence of a mutation of G to T in the first position of codon 905 of PP1 G-subunit coding sequence in a biological sample from said subject according to the method according to claim 4.

17. A kit for detecting the presence of a mutation of G to T in the first position of codon 905 of the gene encoding the PP1 G-subunit, said kit comprising:
(a) a restriction endonuclease which cleaves wild-type PP1 G-subunit DNA at a codon 905-containing recognition site but does not cleave mutant DNA, wherein said mutant DNA contains a G to T mutation in the first position of codon 905 of PP1 G-subunit coding sequence;
(b) a first polynucleotide spanning codon 905 of the PP1 G-subunit that specifically hybridizes to wild-type PP1 G-subunit DNA; and/or
(c) a second polynucleotide spanning codon 905 of the PP1 G-subunit that specifically hybridizes to mutant PP1 G-subunit DNA, wherein said mutant DNA contains a G-T mutation in the first position of codon 905 of PP1 G-subunit coding sequence.

18. The kit according to claim 17, wherein the restriction endonuclease is Dde 1.

19. A kit for detecting the presence of a mutation of G to T in the first position of codon 905 of the gene encoding the PP1 G-subunit, said kit comprising
(a) reagents for amplifying DNA encoding the PP1 G-subunit, and
(b) a labeled oligonucleotide probe spanning codon 905 of PP1 G-subunit coding sequence, wherein said PP1 G-subunit coding sequence contains a G to T mutation in the first position of codon 905, and said probe spedifically hybridizes to the mutant DNA.

20. The test kit according to claim 19, further comprising a labeled oligonucleotide probe spanning codon 905 of the PP1 G-subunit that specifically hybridizes to wild-type PP1 G-subunit DNA.

21. The test kit according to claim 19, wherein the label is selected from the group consisting of enzymes, colored or fluorescent substances, and radioactive isotopes.

22. An isolated variant of the PP1 G-subunit containing a substitution of aspartic acid$^{905}$ by tyrosine, or a fragment thereof containing said substitution.

* * * * *